US009380429B1

(12) United States Patent
Kurani (10) Patent No.: US 9,380,429 B1
(45) Date of Patent: Jun. 28, 2016

(54) SYSTEMS AND METHODS FOR ASSESSING LEVELS OF PERSONAL RISK

(71) Applicant: Symantec Corporation, Mountain View, CA (US)

(72) Inventor: Ankit Kurani, Pune (IN)

(73) Assignee: Symantec Corporation, Mountain View, CA (US)

( * ) Notice: Subject to any disclaimer, the term of this patent is extended or adjusted under 35 U.S.C. 154(b) by 0 days.

(21) Appl. No.: 14/609,456

(22) Filed: Jan. 30, 2015

(51) Int. Cl.
*H04M 11/04* (2006.01)
*H04W 4/02* (2009.01)
*H04L 29/08* (2006.01)
*G06Q 50/26* (2012.01)
*G06F 19/00* (2011.01)
*H04W 4/00* (2009.01)
*H04W 4/22* (2009.01)

(52) U.S. Cl.
CPC ........... *H04W 4/028* (2013.01); *G06F 19/3431* (2013.01); *G06Q 50/265* (2013.01); *H04L 67/12* (2013.01); *H04W 4/008* (2013.01); *H04W 4/22* (2013.01)

(58) Field of Classification Search
CPC .. G06F 19/3431; G06F 19/3418; A61B 5/002
USPC ..................................................... 455/575.8
See application file for complete search history.

(56) References Cited

U.S. PATENT DOCUMENTS

| 2007/0288263 | A1* | 12/2007 | Rodgers | A61B 5/0002 705/2 |
| 2009/0082682 | A1* | 3/2009 | Fischell | A61B 5/0006 600/509 |
| 2013/0095459 | A1* | 4/2013 | Tran | A61B 5/6816 434/247 |
| 2013/0281800 | A1* | 10/2013 | Saroka | A61B 5/00 600/301 |
| 2015/0125832 | A1* | 5/2015 | Tran | G09B 5/00 434/127 |

* cited by examiner

*Primary Examiner* — Thomas Lett
(74) *Attorney, Agent, or Firm* — ALG Intellectual Property, LLC (57) ABSTRACT

A disclosed computer-implemented method for assessing levels of personal risk may include (1) collecting, from a computing system, initial information that describes a user at an initial period of time, (2) determining, based on the initial information, an expected state of the user, (3) receiving, from the computing system, additional information that describes the user at a subsequent period of time after the initial period of time, (4) calculating a risk score by comparing the additional information with the expected state to determine a degree of divergence from the expected state, and (5) performing a safety action based on the risk score. The expected state and/or the additional information may each specify a medical state and/or a location. Various other methods, systems, and computer-readable media are also disclosed.

20 Claims, 7 Drawing Sheets

SYSTEMS AND METHODS FOR ASSESSING LEVELS OF PERSONAL RISK

BACKGROUND

As wearable computing devices become more common, individuals frequently desire a method of tracking the condition and whereabouts of either themselves or others. For example, parents may seek to monitor the whereabouts of their child. Nature enthusiasts may sometimes hike alone in potentially dangerous terrain, but still desire a method of alerting emergency services in the event that they are incapacitated. Traditional tracking methods typically provide a form of location information that computing devices may monitor.

Unfortunately, traditional tracking methods may not provide enough information to determine whether an individual is in danger. Such methods may not account for factors besides location in determining whether an individual is facing a potentially dangerous situation, such as an abnormally elevated heart rate. Further, traditional methods may not account for the fact that a location may be safe during some times but not others. For example, a child might be expected to be on school grounds at 10 AM on a weekday, but not at the same school at midnight. Similarly, an elevated heart rate may not be a sign of risk if the user is at the gym. The instant disclosure, therefore, identifies and addresses a need for additional and improved systems and methods for assessing levels of personal risk.

SUMMARY

As will be described in greater detail below, the instant disclosure describes various systems and methods for assessing levels of personal risk by, for example, comparing information collected about a user to previously collected information and calculating a degree of divergence between the two states. In one example, a method for assessing levels of personal risk may include (1) collecting, from a computing system, initial information that describes a user at an initial period of time, (2) determining an expected state of the user based on the initial information, (3) receiving additional information from the computing system that describes the user at a subsequent period of time after the initial period of time, (4) calculating a risk score by comparing the additional information with the expected state to determine a degree of divergence from the expected state, and (5) performing a safety action based on the risk score. The expected state may include an expected medical state and/or an expected location. Similarly, the additional information may include an additional medical state and/or an additional location. In some embodiments, the medical state may include (1) the user's heart rate, (2) the user's respiratory rate, and/or (3) the user's blood pressure. In other embodiments, the safety action may include (1) requesting medical aid to the user's location, (2) notifying a public safety center, (3) notifying the user, and/or (4) notifying a guardian or representative of the user.

In some embodiments, the initial information may include a list of expected wireless-enabled computing devices that represents wireless-enabled computing devices that are generally found in proximity to the user. The additional information may include a list of discovered wireless-enabled computing devices that represents wireless-enabled computing devices that are discovered in proximity to the user. In some examples, calculating the risk score may include comparing the list of discovered wireless-enabled computing devices to the list of expected wireless-enabled computing devices.

In other embodiments, the computing system may include a smart computing system that tracks the location of the user using (1) a global geo-positioning network, (2) an indoor positioning system, and/or (3) a Wi-Fi-based positioning system. In other examples, the computing system may include a wearable computing system that tracks the medical state of the user.

In some examples, determining the expected state of the user may include extracting a user-annotated event that describes a planned location associated with a planned time. In such examples, extracting the user-annotated event may further include scanning (1) an e-mail inbox, (2) a text-message conversation, and/or (3) social media.

In some embodiments, calculating the risk score may include calculating the risk score based partly on the additional location of the user. In some examples, calculating the risk score may further include comparing the additional information to a risk map that identifies known regions of dangerous activity. In other examples, calculating the risk score may further include determining whether the additional location is a known location. In some examples, calculating the risk score may include calculating the risk score based partly on the additional medical state of the user. In other examples, calculating the risk score may include (1) calculating the expected heart rate of the user by determining an average heart rate and (2) determining a degree of divergence between the additional medical state of the user and the average heart rate.

In one embodiment, a system for implementing the above-described method may include (1) a collection module, stored in memory, that collects, from a computing system, initial information that describes a user at an initial period of time, (2) a determination module, stored in memory, that determines an expected state of the user based on the initial information, (3) a reception module, stored in memory, that receives additional information from the computing system that describes the user at a subsequent period of time after the initial period of time, (4) a calculation module, stored in memory, that calculates a risk score by comparing the additional information with the expected state to determine a degree of divergence from the expected state, (5) a safety module, stored in memory, that performs a safety action based on the risk score, and (6) at least one physical processor configured to execute the collection module, the determination module, the reception module, the calculation module, and the safety module.

In some examples, the above-described method may be encoded as computer-readable instructions on a non-transitory computer-readable medium. For example, a computer-readable medium may include one or more computer-executable instructions that, when executed by at least one processor of a computing device, may cause the computing device to (1) collect, from a computing system, initial information that describes a user at an initial period of time, (2) determine an expected state of the user based on the initial information, (3) receive additional information from the computing system that describes the user at a subsequent period of time after the initial period of time, (4) calculate a risk score by comparing the additional information with the expected state to determine a degree of divergence from the expected state, and (5) perform a safety action based on the risk score.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to systems and methods for assessing levels of personal risk. As will be explained in greater detail below, collecting location, medical, and/or other information about a user and then comparing the collected information to previously collected information or a previously established baseline may enable systems described herein to accurately determine if the user is at risk for injury or harm. Moreover, systems and methods herein may enable such risk assessment to be performed with greater accuracy than traditional methods that fail to account for location or medical state.

Figure 1:
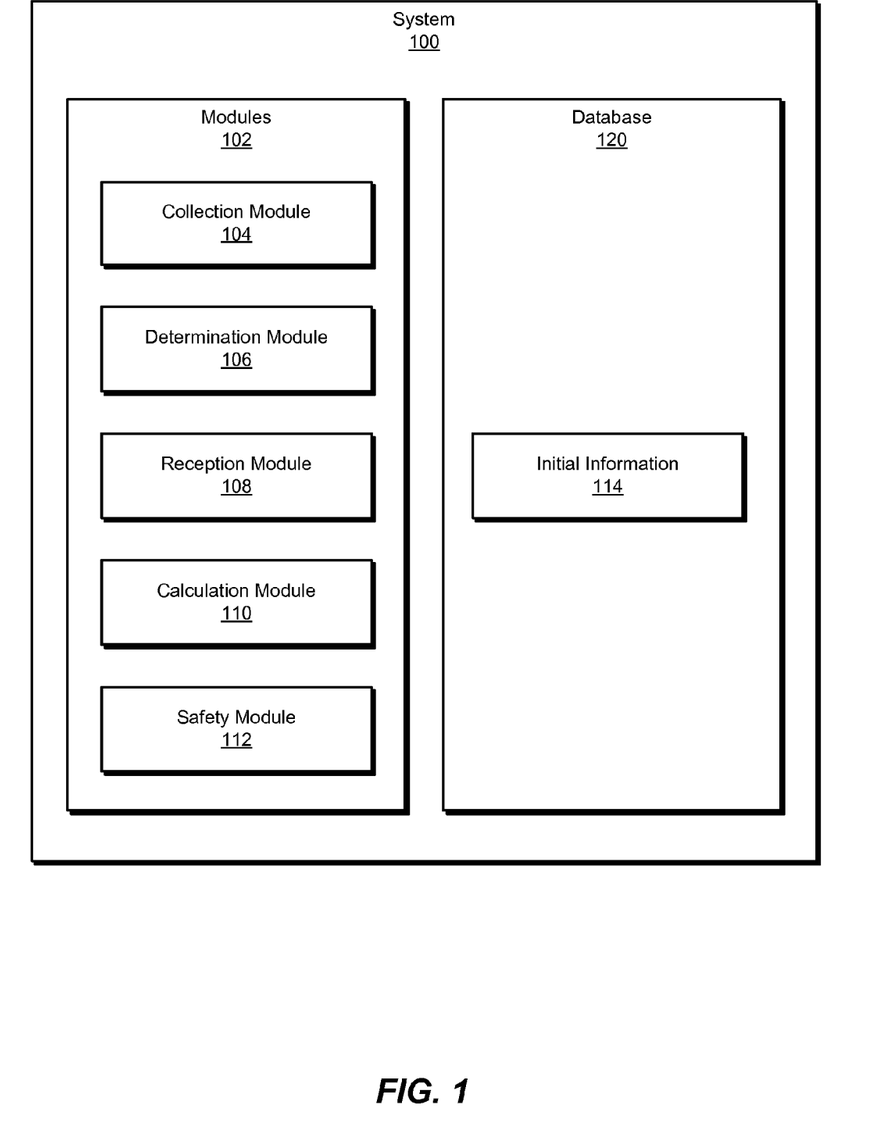
FIG. 1 is a block diagram of an exemplary system for assessing levels of personal risk.
Figure 2:
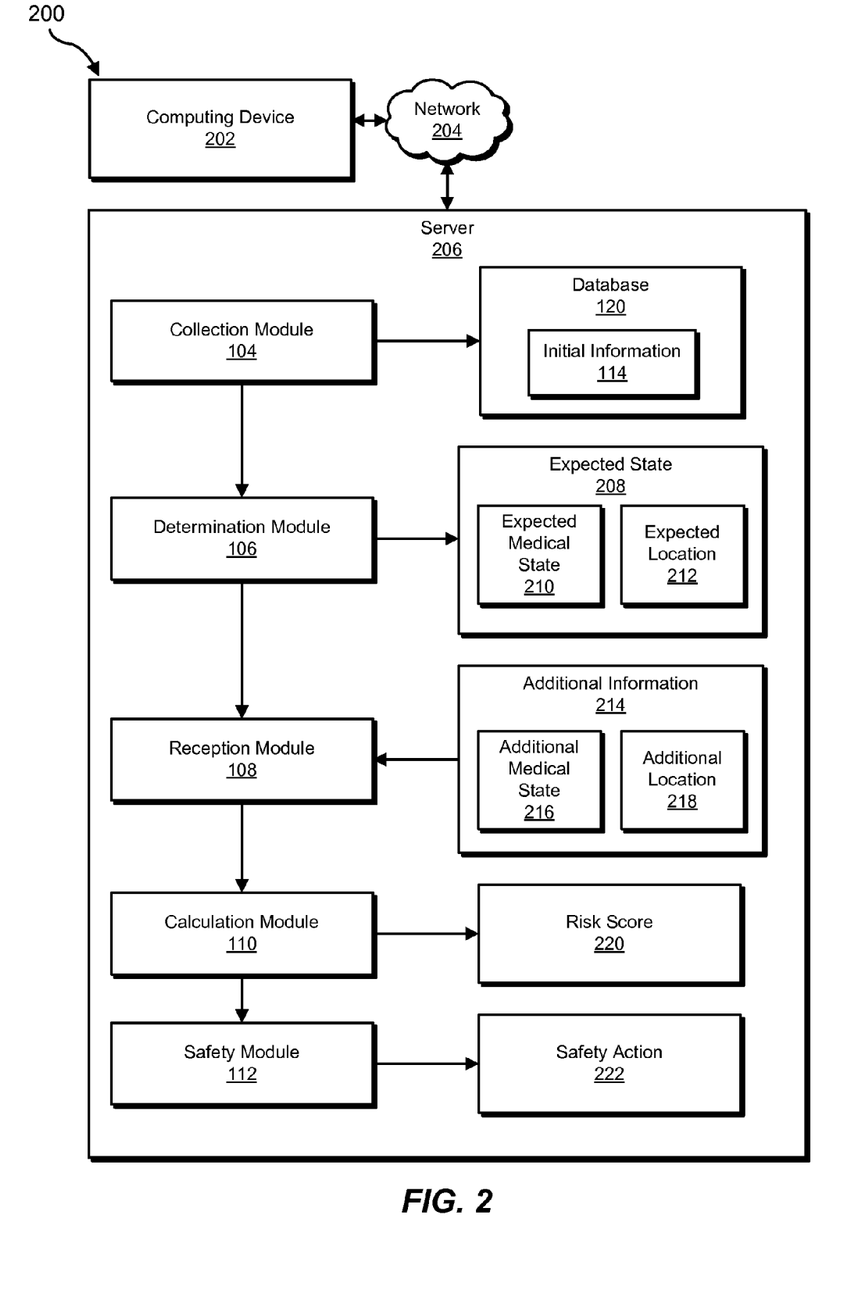
FIG. 2 is a block diagram of an additional exemplary system for assessing levels of personal risk.

The following will provide, with reference to FIGS. 1 and 2, detailed descriptions of exemplary systems for assessing levels of personal risk. Detailed descriptions of corresponding computer-implemented methods will also be provided in connection with FIGS. 3-5. In addition, detailed descriptions of an exemplary computing system and network architecture capable of implementing one or more of the embodiments described herein will be provided in connection with FIGS. 6 and 7, respectively.

FIG. 1 is a block diagram of exemplary system 100 for assessing levels of personal risk. As illustrated in this figure, exemplary system 100 may include one or more modules 102 for performing one or more tasks. For example, and as will be explained in greater detail below, exemplary system 100 may include a collection module 104 that may collect, from a computing system, initial information 114 that describes a user at an initial period of time. Exemplary system 100 may additionally include a determination module 106 that may determine an expected state of the user based partly or entirely on the initial information. The expected state may include an expected medical state and/or an expected location. Exemplary system 100 may further include a reception module 108 that may receive additional information that describes the user at a subsequent period of time after the initial period of time from the set of computing systems. Moreover, exemplary system 100 may include a calculation module 110 that may calculate a risk score by comparing the additional information with the expected state to determine a degree of divergence from the expected state. Exemplary system 100 may further include a safety module 112 that may perform a safety action based on the risk score. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, and as will be described in greater detail below, one or more of modules 102 may represent software modules stored and configured to run on one or more computing devices, such as the devices illustrated in FIG. 2 (e.g., computing device 202 and/or server 206), computing system 610 in FIG. 6, and/or portions of exemplary network architecture 700 in FIG. 7. One or more of modules 102 in FIG. 1 may also represent all or portions of one or more special-purpose computers configured to perform one or more tasks.

As illustrated in FIG. 1, exemplary system 100 may also include one or more databases, such as database 120. In one example, database 120 may be configured to store medical information and/or location information that describes the state of a user, such as initial information 114. In other examples, database 120 may be configured to store the medical information and/or location information in association with time information (e.g., timestamps or generalized times of day).

Database 120 may represent portions of a single database or computing device or a plurality of databases or computing devices. For example, database 120 may represent a portion of server 206 in FIG. 2, computing system 610 in FIG. 6, and/or portions of exemplary network architecture 700 in FIG. 7. Alternatively, database 120 in FIG. 1 may represent one or more physically separate devices capable of being accessed by a computing device, such as server 206 in FIG. 2, computing system 610 in FIG. 6, and/or portions of exemplary network architecture 700 in FIG. 7.

Exemplary system 100 in FIG. 1 may be implemented in a variety of ways. For example, all or a portion of exemplary system 100 may represent portions of exemplary system 200 in FIG. 2. As shown in FIG. 2, system 200 may include a computing device 202 in communication with a server 206 via a network 204. In one example, computing device 202 may be programmed with one or more of modules 102 and/or may store all or a portion of the data in database 120. Additionally or alternatively, server 206 may be programmed with one or more of modules 102 and/or may store all or a portion of the data in database 120.

In one embodiment, one or more of modules 102 from FIG. 1 may, when executed by at least one processor of computing device 202 and/or server 206, enable computing device 202 and/or server 206 to assess levels of personal risk. For example, and as will be described in greater detail below, collection module 104 may collect initial information 114 from computing device 202 and store all or a portion of initial information 114 in database 120. Initial information 114 may describe a user at an initial period of time. Determination module 106 may determine, based on initial information 114, an expected state 208 of the user. Expected state 208 may include an expected medical state 210 and/or an expected location 212. Reception module 108 may receive additional information 214 from computing device 202. Additional information 214 may describe the user at a subsequent period of time after the initial period of time. Additional information 214 may include an additional medical state 216 and/or an additional location 218. Calculation module 110 may calculate a risk score 220 by comparing additional information 214 with expected state 208 to determine a degree of divergence from expected state 208. Safety module 112 may perform a safety action 222 based on risk score 220.

Computing device 202 generally represents any type or form of computing device or set of computing devices capable of reading computer-executable instructions. Examples of computing device 202 include, without limitation, laptops, tablets, desktops, servers, cellular phones, Personal Digital Assistants (PDAs), multimedia players, embedded systems, wearable devices (e.g., smart watches, smart glasses, etc.), gaming consoles, combinations of one or more of the same, exemplary computing system 610 in FIG. 6, or any other suitable computing device.

Server 206 generally represents any type or form of computing device that is capable of collecting information that describes the location and/or the medical state of a user. Additionally, server 206 may be capable of comparing the collected information to previously collected information that describes the location and/or the medical state of the user. Examples of server 206 include, without limitation, application servers and database servers configured to provide various database services and/or run certain software applications.

Network 204 generally represents any medium or architecture capable of facilitating communication or data transfer. Examples of network 204 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), exemplary network architecture 700 in FIG. 7, or the like. Network 204 may facilitate communication or data transfer using wireless or wired connections. In one embodiment, network 204 may facilitate communication between computing device 202 and server 206.

Figure 3:
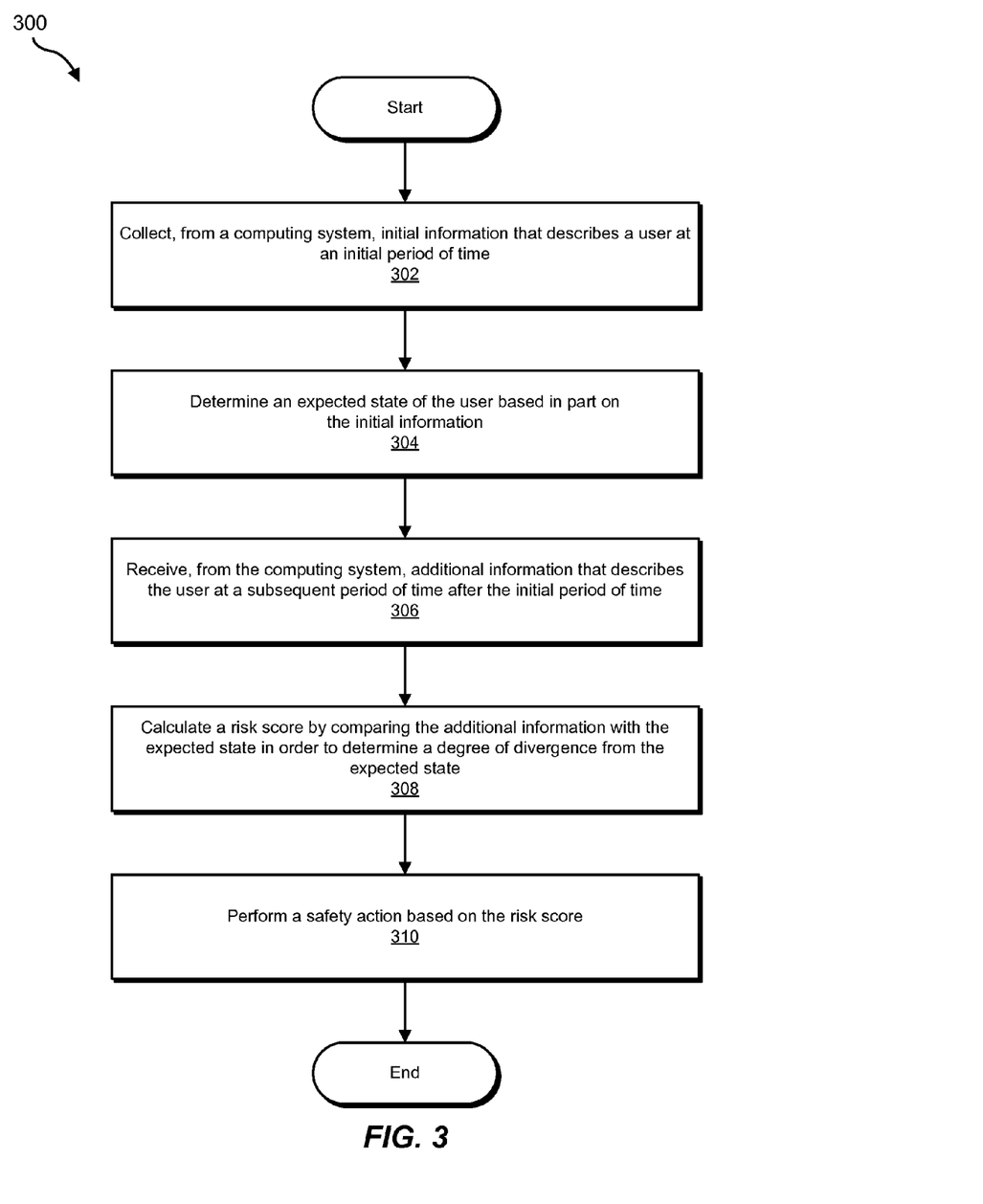
FIG. 3 is a flow diagram of an exemplary method for assessing levels of personal risk.

FIG. 3 is a flow diagram of an exemplary computer-implemented method 300 for assessing levels of personal risk. The steps shown in FIG. 3 may be performed by any suitable computer-executable code and/or computing system. In some embodiments, the steps shown in FIG. 3 may be performed by one or more of the components of system 100 in FIG. 1, system 200 in FIG. 2, computing system 610 in FIG. 6, and/or portions of exemplary network architecture 700 in FIG. 7.

As illustrated in FIG. 3, at step 302, one or more of the systems described herein may collect initial information that describes a user at an initial period of time from a set of computing systems. For example, collection module 104 may, as part of server 206 in FIG. 2, collect, from computing device 202, initial information 114 that describes a user at an initial period of time.

Collection module 104 may collect a variety of information as part of initial information 114. In some examples, collection module 104 may collect information that describes a medical state of the user. In other examples, computing device 202 may track the location of the user. In these examples, computing device 202 may track the location of the user in a variety of ways, including but not limited to a global geo-positioning network, an indoor positioning system, and/or a Wi-Fi based positioning system. In further examples, collection module 104 may identify a list of wireless-enabled computing devices found in proximity to the user. A wireless-enabled computing device may represent a personal computing device (e.g., cell phones, smart watches, etc.) carried by individuals. Alternatively, a wireless-enabled computing device may be linked to a location (e.g., wireless router, wireless-enabled personal computer, game console, smart television, etc.). Moreover, collection module 104 may collect time information in association with any or all of the above elements of information. As will be described in greater detail below, different times may correspond to different expected states.

The term "medical state," as used herein, generally refers to information that describes a user's physiological state. Examples of a medical state include, without limitation, heart rate, respiratory rate, blood pressure, blood glucose level, combinations of one or more of the same, or any other suitable information that describes a user's physiological state.

The terms "smart computing system" and "smart device," as used herein, generally refer to any computing device that contains one or more processors designed to execute computer-readable instructions. Examples of smart computing devices include, without limitation, cellular phones, Personal Digital Assistants (PDAs), embedded systems, wearable devices (e.g., smart watches, smart glasses, etc.), gaming consoles, combinations of one or more of the same, or any other suitable computing device.

Collection module 104 may collect initial information 114 in a variety of ways. In some examples, computing device 202 may represent a set of computing systems. In some embodiments, collection module 104 may collect initial information 114 from each computing system individually. In other embodiments, collection module 104 may operate as part of a single (e.g., master) computing system and collect initial information 114 from other computing systems connected to the single computing system. The systems may be connected in a variety of ways, including but not limited to physical connections, personal area networks, body area networks, combinations of one or more of the same, or any other suitable connection. In further examples, collection module 104 may collect initial information 114 from a single computing system that may collect parts of the initial information from other computing systems in the set of computing systems. In some embodiments, collection module 104 may collect initial information 114 over a period of time. Various elements of information such as location, medical state, etc., may be collected in association with times and dates to create a profile of expected states that evolves to more accurately reflect various expected states of the user as more information is collected.

Figure 4:
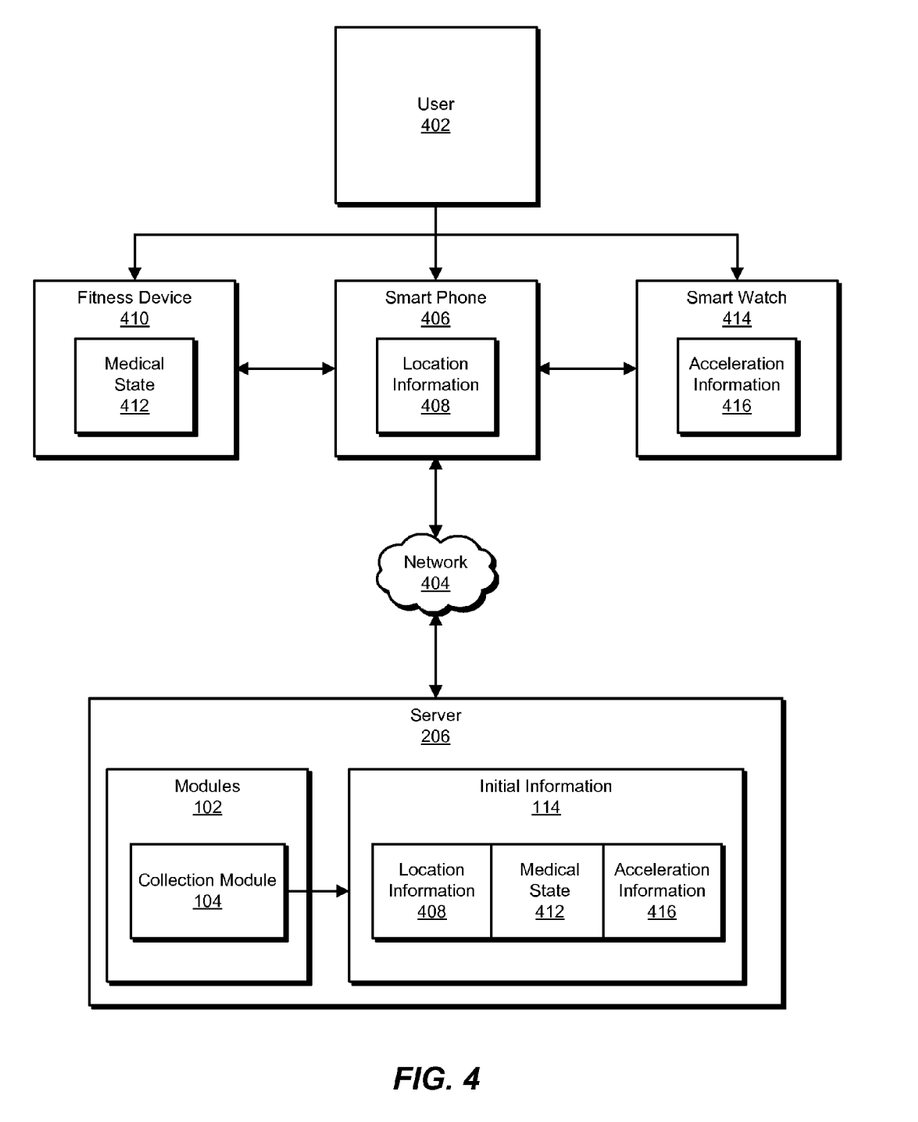
FIG. 4 is a block diagram of an exemplary computing system for collecting information that describes the state of a user.

FIG. 4 is a block diagram of an exemplary system for collecting information that describes the state of a user from a set of computing systems. A user 402 may wear a fitness device 410 that tracks a medical state 412 of user 402, and a smart watch 414 that measures acceleration information 416. Acceleration information 416 may take a variety of forms, such as information from a pedometer function that tracks the rate at which user 402 is walking or running. User 402 may also carry a smart phone 406 that may communicate with Wi-Fi network infrastructure and/or a global geo-positioning system to generate location information 408. As described above, smart phone 406 may be connected to and collect information from fitness device 410 and smart watch 414 through a variety of means, including but not limited to a personal area network such as BLUETOOTH. Collection module 104 may, as part of modules 102 running on server 206, collect location information 408, medical state 412, and acceleration information 416 from one or more of fitness device 410, smart phone 406, and/or smart watch 414, via a network 404. In other words, in some examples, one or more of the devices that the user possesses or wears may collect information from one or more remaining devices and then transmit that information to server 206. Collection module 104 may then store location information 408, medical state 412, and acceleration information 416 as part of initial information 114.

Returning to FIG. 3 at step 304, one or more of the systems described herein may determine an expected state of the user based on the initial information. For example, determination module 106 may, as part of server 206 in FIG. 2, determine expected state 208 of the user based in part on initial information 114. Expected state 208 may include expected medical state 210 and/or expected location 212.

Determination module 106 may determine the expected state of the user based in part on initial information 114. In some examples, determination module 106 may determine expected state 208 of the user based on multiple sets of initial information, gathered at various points in time. For example, initial information 114 may contain heart rate information tracked over several days. In some embodiments, determination module 106 may determine an expected heart rate based on the tracked information, such as by determining an average heart rate. Moreover, initial information 114 may link an expected medical state to an expected location and/or a time of day. For example, a user's heart rate is typically lower when they are asleep at home versus when they are awake at work. Further, the user may have particular routines that result in an elevated heart rate at a given location, such as a daily trip to the gym. As such, determination module 106 may determine a different expected medical state for different times of day, days of the week, or any other suitable period of time. Similarly, determination module 106 may also determine a different expected medical state for different locations.

In some embodiments, initial information 114 may contain a map and/or list of expected locations and/or a set of regions that indicate safe or known locations (or, alternatively, dangerous locations or locations with known criminal activity). For example, a child might be expected to be safer at home, at school, or at the library versus a non-designated safe space. Initial information 114 may accordingly include a list of known locations such as home, school, and/or the library. Determination module 106 may also identify different expected locations based on the time of day. For example, a school might be an expected location for a child during the day, but not the middle of the night. Initial information 114 may accordingly link known locations to times when the location might be expected, such as a school being flagged as an expected location during the day, but flagged as unexpected at night.

In further embodiments, determination module 106 may determine expected state 208 by extracting a user-annotated event that describes a planned location associated with a planned time. In some embodiments, determination module 106 may extract the user-annotated event by scanning an e-mail inbox, a text-message conversation, and/or social media. Determination module 106 may use text pattern analysis to extract relevant information, such as date, time, and/or location, from the user-annotated event. Determination module 106 may modify or add to an expected state based on the information extracted from the user-annotated event.

Returning to FIG. 3 at step 306, one or more of the systems described herein may receive, from the set of computing systems, additional information that describes the user at a subsequent period of time after the initial period of time. The additional information may include an additional medical state and/or an additional location. For example, reception module 108 may, as part of server 206 in FIG. 2, receive, from computing device 202, additional information 214 that describes the user at a subsequent period of time after the initial period of time. Additional information 214 may include additional medical state 216 and/or additional location 218.

Reception module 108 may receive the additional information in a variety of ways, which are similar to the ways described above in connection with collection module 104. For example, reception module 108 may receive separate elements of additional information 214 from individual computing devices. Additionally or alternatively, reception module 108 may receive the entirety of additional information 214 from a single computing device that collects individual elements of additional information from the set of computing devices. In some embodiments, reception module 108 may receive time information as part of additional information 214 that describes the time at which the computing devices generated additional information 214. Calculation module 110 may use additional information 214 to calculate risk score 220, as discussed below.

As illustrated in FIG. 3 at step 308, one or more of the systems described herein may calculate a risk score by comparing the additional information with the expected state to determine a degree of divergence from the expected state. For example, calculation module 110 may, as part of server 206 in FIG. 2, calculate risk score 220 by comparing additional information 214 with expected state 208 to determine a degree of divergence from expected state 208.

Risk score 220 generally represents an overall level of risk experienced by the user. This risk may take a variety of forms, such as the user experiencing abnormal heart rate, experiencing an abnormal heart rate for a given location, being in an unexpected location, not being at a planned location, and/or any other state that deviates from the expected state. Calculation module 110 may calculate risk score 220 based on degrees of divergence for each element of the user's state, such as expected heart rate, expected location, expected wireless-enabled computing devices, extracted information from electronic documents and social media (as discussed above), and/or any other information collected as part of initial information 114 and/or additional information 214. Risk score 220 may be a single value that represents an aggregate summary of the degrees of deviation. In other words, risk score 220 may reflect a binary or granular score, as an output, based on underlying inputs that indicate medical states, location information, wireless and network node surroundings, and/or information extracted from electronic documents and social media. Calculation module 110 may calculate risk score 220 using any weighted or non-weighted Boolean, business, and/or algebraic formula or algorithm. In some examples, one or more of modules 102, such as calculation module 110, may compare an initial value with a threshold to determine whether the threshold is satisfied (and, therefore, that a safety action should be performed). In these cases, risk score 220 may represent either the input or the output of this comparison.

In some embodiments, calculation module 110 may calculate the risk score by calculating the risk score based in part on the additional location of the user. For example, calculation module 110 may calculate the risk score by comparing the additional information to a risk map that identifies known regions of dangerous activity. The risk map may be included as part of initial information 114. Additionally or alternatively, the risk map may be provided by a third party. Examples of known dangerous activity may include, without limitation, construction sites, areas of known criminal activity, chemical spills, or any other situation that may present a hazard to the well-being of a user.

In other embodiments, calculation module 110 may calculate the risk score in part by determining whether the additional location is a known location. For example, initial information 114 may contain information that identifies locations in which the user habitually spends time, such as home, work, a gym, etc. Such locations may accordingly be treated as known locations. Calculation module 110 may compare additional location 218 to information contained in initial information 114. Calculation module 110 may modify risk score 220 based on whether additional location 218 matches a known location. In other embodiments, calculation module 110 may also modify risk score 220 based on how far the user is from a known location.

In some examples, calculation module 110 may calculate the risk score based at least in part on the additional medical state of the user. For example, calculation module 110 may identify additional heart rate information contained in additional medical state 216 and compare the additional heart rate to expected heart rate information contained in expected medical state 210. Calculation module 110 may modify risk score 220 based on the difference between the additional heart rate and the expected heart rate. Calculation module 110 may similarly determine degrees of divergence for other medical states recorded as part of additional medical state 216 (which may include any physiological measurement, such as heart rate, blood pressure, brain activity, muscle activity, facial movements and twitches, exercise, temperature, vocal tone and activity, and/or impaired breathing, etc.).

In other examples, calculation module 110 may calculate the risk score in part by comparing the list of discovered wireless-enabled computing devices to the list of expected wireless-enabled computing devices. As discussed above, the presence of an expected wireless-enabled computing device may indicate the presence of known or trusted individuals. Alternatively, an expected wireless-enabled computing device may indicate a particular expected building or room, such as a public library. Conversely, the presence of unexpected wireless-enabled computing devices may indicate the presence of unknown or untrusted individuals, or represent an unexpected location. Calculation module 110 may modify risk score 220 based on the list of discovered wireless-enabled computing devices in a variety of ways. For example, calculation module 110 may calculate risk score 220 based on a ratio of expected wireless-enabled computing devices to unexpected wireless-enabled computing devices. Calculation module 110 may additionally or alternatively calculate risk score 220 based on whether the number of unexpected wireless-enabled computing devices exceeds a predetermined threshold.

Figure 5:
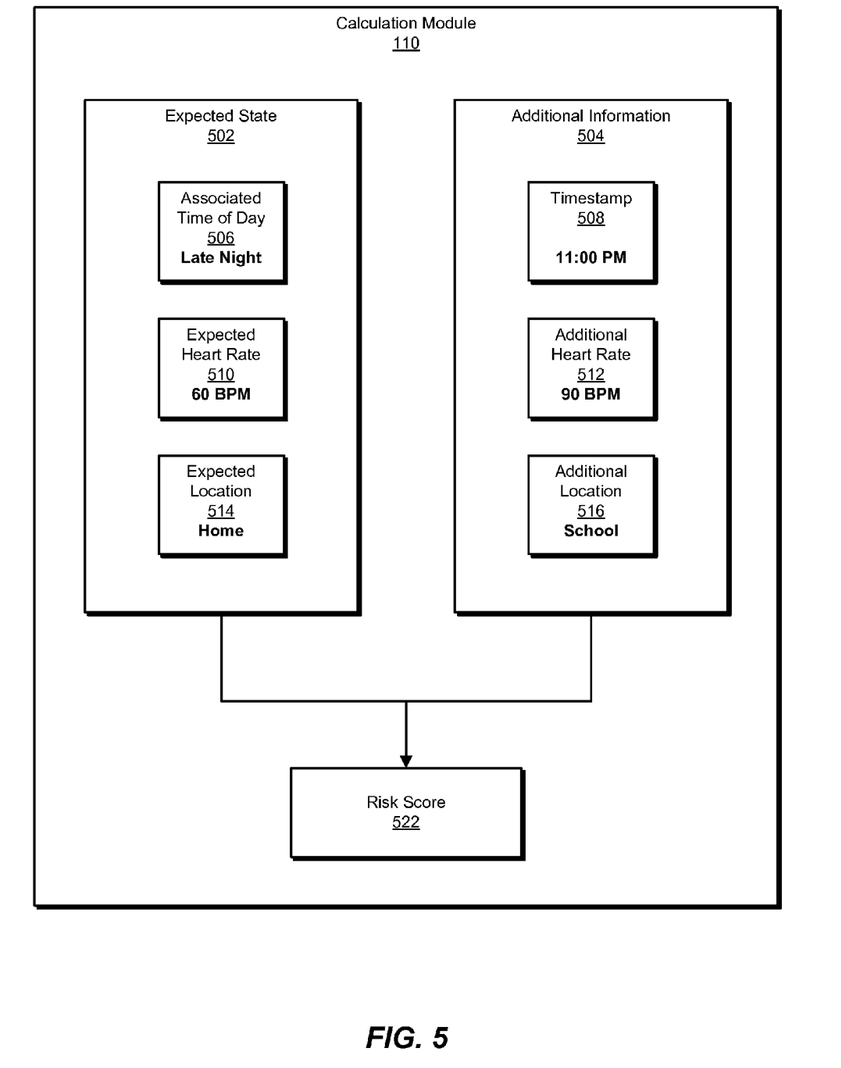
FIG. 5 is a block diagram of an exemplary system for determining a risk score by comparing an expected state to a current state.

FIG. 5 is a block diagram of an exemplary system for calculating a risk score by comparing additional information to an expected state. Calculation module 110 may compare additional information 504 to an expected state 502. Additional information describes an additional heart rate 512 and an additional location 516 in connection with a timestamp 508 that describes the time at which additional heart rate 512 and additional location 516 were collected. Expected state 502 describes an expected heart rate 510 and an expected location 514 in connection with an associated time of day 506. Calculation module 110 may compare each element of additional information 504 to the corresponding element of expected state 502. Calculation module 110 may identify that the time of 11:00 PM contained in timestamp 508 corresponds to the general time of day, "late night," contained in associated time of day 506 and accordingly determine that it is valid to compare additional information 504 to expected state 502. An invalid comparison may include comparing additional information 504 to an expected state associated with the time of day, "early morning." Calculation module 110 may compare additional heart rate 512 (90 BPM) to expected heart rate 510 (60 BPM). Because additional heart rate 512 is significantly greater than expected heart rate 510, calculation module 110 may accordingly adjust a risk score 522 to indicate that the user may be experiencing an abnormally elevated heart rate. Calculation module 110 may further compare additional location 516 ("School") to expected location 514 ("Home"). In this example, the user is currently located at school when they are expected to be at home. Calculation module 110 may accordingly adjust risk score 522 to account for the fact that the user is not at or near expected location 514. Because both additional location 516 and additional heart rate 512 diverge significantly from expected state 502, risk score 522 may represent a situation in which one or more of the systems described herein should undertake a safety action.

In other words, both additional location 516 and additional heart rate 512 may each result in calculated degrees of divergence. Moreover, calculation module 110 may use these calculated degrees of divergence as inputs into a formula for calculating risk score 220 as an overall representation of calculated risk (e.g., any weighted or non-weighted formula that computes an average, median, composite, and/or summary score based on underlying degrees of divergence). Additionally, calculation module 110 or another module may compare calculated risk score 220 to a threshold and determined that the threshold is satisfied, because both of the inputs indicate significant divergences from the expected state.

Returning to FIG. 3 at step 310, one or more of the systems described herein may perform a safety action based on the risk score. For example, safety module 112 may, as part of server 206 in FIG. 2, perform safety action 222 based on risk score 220.

Safety module 112 may perform a variety of safety actions. Safety module 112 may perform actions such as requesting medical aid to the user's location, notifying a public safety center that the user is in danger, notifying the user that the user is in danger, notifying a guardian or representative of the user that the user is in danger, or any other suitable action based on the risk score.

Safety module 112 may perform different safety actions depending on which elements of the additional information diverge from the expected state. In some embodiments, safety module 112 may request medical aid to the user's location if additional medical state 216 diverges significantly from expected medical state 210. Safety module 112 may request medical aid to the user's location in this situation, even if additional location 218 does not significantly diverge from expected location 212. In another example, safety module 112 may notify a guardian or representative of the user if additional location 218 diverges significantly from expected location 212, even if additional medical state 216 does not diverge from expected medical state 210.

As described above, collecting location, medical, and/or other information about a user, then comparing the collected information to previously collected information or a previously established baseline may enable systems described herein to accurately determine if the user is at risk for injury or harm. Moreover, systems and methods herein may enable such risk assessment to be performed with a finer level of granularity than traditional methods that fail to account for location and/or medical state.

Figure 6:
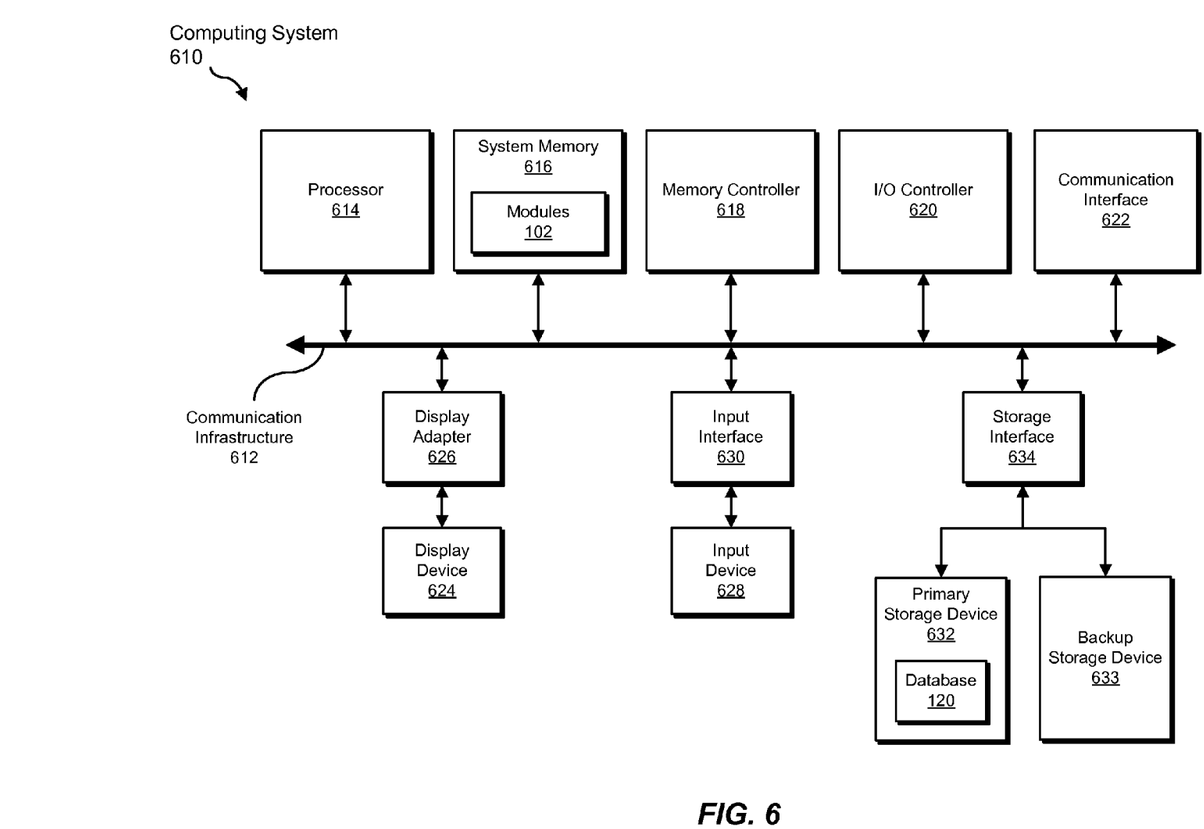
FIG. 6 is a block diagram of an exemplary computing system capable of implementing one or more of the embodiments described and/or illustrated herein.

FIG. 6 is a block diagram of an exemplary computing system 610 capable of implementing one or more of the embodiments described and/or illustrated herein. For example, all or a portion of computing system 610 may perform and/or be a means for performing, either alone or in combination with other elements, one or more of the steps described herein (such as one or more of the steps illustrated in FIG. 3). All or a portion of computing system 610 may also perform and/or be a means for performing any other steps, methods, or processes described and/or illustrated herein.

Computing system 610 broadly represents any single or multi-processor computing device or system capable of executing computer-readable instructions. Examples of computing system 610 include, without limitation, workstations, laptops, client-side terminals, servers, distributed computing systems, handheld devices, or any other computing system or device. In its most basic configuration, computing system 610 may include at least one processor 614 and a system memory 616.

Processor 614 generally represents any type or form of physical processing unit (e.g., a hardware-implemented central processing unit) capable of processing data or interpreting and executing instructions. In certain embodiments, processor 614 may receive instructions from a software application or module. These instructions may cause processor 614 to perform the functions of one or more of the exemplary embodiments described and/or illustrated herein.

System memory 616 generally represents any type or form of volatile or non-volatile storage device or medium capable of storing data and/or other computer-readable instructions. Examples of system memory 616 include, without limitation, Random Access Memory (RAM), Read Only Memory (ROM), flash memory, or any other suitable memory device. Although not required, in certain embodiments computing system 610 may include both a volatile memory unit (such as, for example, system memory 616) and a non-volatile storage device (such as, for example, primary storage device 632, as described in detail below). In one example, one or more of modules 102 from FIG. 1 may be loaded into system memory 616.

In certain embodiments, exemplary computing system 610 may also include one or more components or elements in addition to processor 614 and system memory 616. For example, as illustrated in FIG. 6, computing system 610 may include a memory controller 618, an Input/Output (I/O) controller 620, and a communication interface 622, each of which may be interconnected via a communication infrastructure 612. Communication infrastructure 612 generally represents any type or form of infrastructure capable of facilitating communication between one or more components of a computing device. Examples of communication infrastructure 612 include, without limitation, a communication bus (such as an Industry Standard Architecture (ISA), Peripheral Component Interconnect (PCI), PCI Express (PCIe), or similar bus) and a network.

Memory controller 618 generally represents any type or form of device capable of handling memory or data or controlling communication between one or more components of computing system 610. For example, in certain embodiments memory controller 618 may control communication between processor 614, system memory 616, and I/O controller 620 via communication infrastructure 612.

I/O controller 620 generally represents any type or form of module capable of coordinating and/or controlling the input and output functions of a computing device. For example, in certain embodiments I/O controller 620 may control or facilitate transfer of data between one or more elements of computing system 610, such as processor 614, system memory 616, communication interface 622, display adapter 626, input interface 630, and storage interface 634.

Communication interface 622 broadly represents any type or form of communication device or adapter capable of facilitating communication between exemplary computing system 610 and one or more additional devices. For example, in certain embodiments communication interface 622 may facilitate communication between computing system 610 and a private or public network including additional computing systems. Examples of communication interface 622 include, without limitation, a wired network interface (such as a network interface card), a wireless network interface (such as a wireless network interface card), a modem, and any other suitable interface. In at least one embodiment, communication interface 622 may provide a direct connection to a remote server via a direct link to a network, such as the Internet. Communication interface 622 may also indirectly provide such a connection through, for example, a local area network (such as an Ethernet network), a personal area network, a telephone or cable network, a cellular telephone connection, a satellite data connection, or any other suitable connection.

In certain embodiments, communication interface 622 may also represent a host adapter configured to facilitate communication between computing system 610 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 622 may also allow computing system 610 to engage in distributed or remote computing. For example, communication interface 622 may receive instructions from a remote device or send instructions to a remote device for execution.

As illustrated in FIG. 6, computing system 610 may also include at least one display device 624 coupled to communication infrastructure 612 via a display adapter 626. Display device 624 generally represents any type or form of device capable of visually displaying information forwarded by display adapter 626. Similarly, display adapter 626 generally represents any type or form of device configured to forward graphics, text, and other data from communication infrastructure 612 (or from a frame buffer, as known in the art) for display on display device 624.

As illustrated in FIG. 6, exemplary computing system 610 may also include at least one input device 628 coupled to communication infrastructure 612 via an input interface 630.

Input device 628 generally represents any type or form of input device capable of providing input, either computer or human generated, to exemplary computing system 610. Examples of input device 628 include, without limitation, a keyboard, a pointing device, a speech recognition device, or any other input device.

As illustrated in FIG. 6, exemplary computing system 610 may also include a primary storage device 632 and a backup storage device 633 coupled to communication infrastructure 612 via a storage interface 634. Storage devices 632 and 633 generally represent any type or form of storage device or medium capable of storing data and/or other computer-readable instructions. For example, storage devices 632 and 633 may be a magnetic disk drive (e.g., a so-called hard drive), a solid state drive, a floppy disk drive, a magnetic tape drive, an optical disk drive, a flash drive, or the like. Storage interface 634 generally represents any type or form of interface or device for transferring data between storage devices 632 and 633 and other components of computing system 610. In one example, database 120 from FIG. 1 may be stored in primary storage device 632.

In certain embodiments, storage devices 632 and 633 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 632 and 633 may also include other similar structures or devices for allowing computer software, data, or other computer-readable instructions to be loaded into computing system 610. For example, storage devices 632 and 633 may be configured to read and write software, data, or other computer-readable information. Storage devices 632 and 633 may also be a part of computing system 610 or may be a separate device accessed through other interface systems.

Many other devices or subsystems may be connected to computing system 610. Conversely, all of the components and devices illustrated in FIG. 6 need not be present to practice the embodiments described and/or illustrated herein. The devices and subsystems referenced above may also be interconnected in different ways from that shown in FIG. 6. Computing system 610 may also employ any number of software, firmware, and/or hardware configurations. For example, one or more of the exemplary embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 610. All or a portion of the computer program stored on the computer-readable medium may then be stored in system memory 616 and/or various portions of storage devices 632 and 633. When executed by processor 614, a computer program loaded into computing system 610 may cause processor 614 to perform and/or be a means for performing the functions of one or more of the exemplary embodiments described and/or illustrated herein. Additionally or alternatively, one or more of the exemplary embodiments described and/or illustrated herein may be implemented in firmware and/or hardware. For example, computing system 610 may be configured as an Application Specific Integrated Circuit (ASIC) adapted to implement one or more of the exemplary embodiments disclosed herein.

Figure 7:
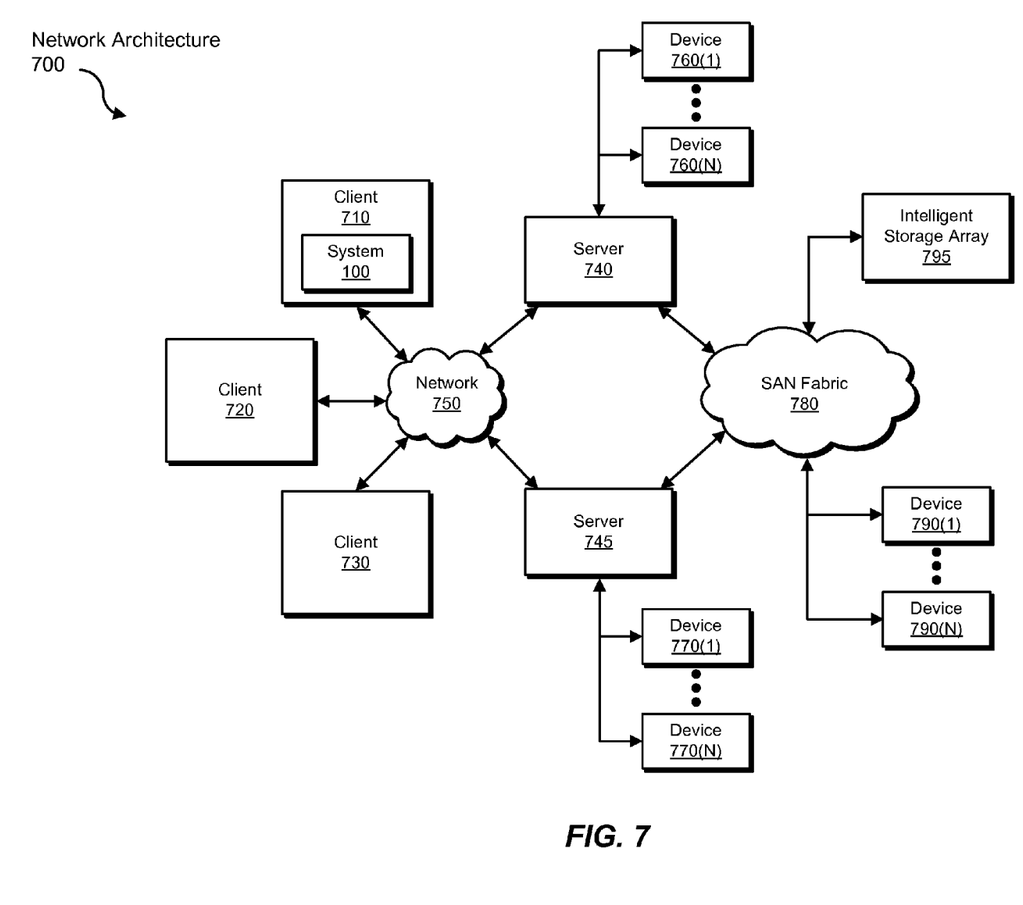
FIG. 7 is a block diagram of an exemplary computing network capable of implementing one or more of the embodiments described and/or illustrated herein.

FIG. 7 is a block diagram of an exemplary network architecture 700 in which client systems 710, 720, and 730 and servers 740 and 745 may be coupled to a network 750. As detailed above, all or a portion of network architecture 700 may perform and/or be a means for performing, either alone or in combination with other elements, one or more of the steps disclosed herein (such as one or more of the steps illustrated in FIG. 3). All or a portion of network architecture 700 may also be used to perform and/or be a means for performing other steps and features set forth in the instant disclosure.

Client systems 710, 720, and 730 generally represent any type or form of computing device or system, such as exemplary computing system 610 in FIG. 6. Similarly, servers 740 and 745 generally represent computing devices or systems, such as application servers or database servers, configured to provide various database services and/or run certain software applications. Network 750 generally represents any telecommunication or computer network including, for example, an intranet, a WAN, a LAN, a PAN, or the Internet. In one example, client systems 710, 720, and/or 730 and/or servers 740 and/or 745 may include all or a portion of system 100 from FIG. 1.

As illustrated in FIG. 7, one or more storage devices 760(1)-(N) may be directly attached to server 740. Similarly, one or more storage devices 770(1)-(N) may be directly attached to server 745. Storage devices 760(1)-(N) and storage devices 770(1)-(N) generally represent any type or form of storage device or medium capable of storing data and/or other computer-readable instructions. In certain embodiments, storage devices 760(1)-(N) and storage devices 770(1)-(N) may represent Network-Attached Storage (NAS) devices configured to communicate with servers 740 and 745 using various protocols, such as Network File System (NFS), Server Message Block (SMB), or Common Internet File System (CIFS).

Servers 740 and 745 may also be connected to a Storage Area Network (SAN) fabric 780. SAN fabric 780 generally represents any type or form of computer network or architecture capable of facilitating communication between a plurality of storage devices. SAN fabric 780 may facilitate communication between servers 740 and 745 and a plurality of storage devices 790(1)-(N) and/or an intelligent storage array 795. SAN fabric 780 may also facilitate, via network 750 and servers 740 and 745, communication between client systems 710, 720, and 730 and storage devices 790(1)-(N) and/or intelligent storage array 795 in such a manner that devices 790(1)-(N) and array 795 appear as locally attached devices to client systems 710, 720, and 730. As with storage devices 760(1)-(N) and storage devices 770(1)-(N), storage devices 790(1)-(N) and intelligent storage array 795 generally represent any type or form of storage device or medium capable of storing data and/or other computer-readable instructions.

In certain embodiments, and with reference to exemplary computing system 610 of FIG. 6, a communication interface, such as communication interface 622 in FIG. 6, may be used to provide connectivity between each client system 710, 720, and 730 and network 750. Client systems 710, 720, and 730 may be able to access information on server 740 or 745 using, for example, a web browser or other client software. Such software may allow client systems 710, 720, and 730 to access data hosted by server 740, server 745, storage devices 760(1)-(N), storage devices 770(1)-(N), storage devices 790(1)-(N), or intelligent storage array 795. Although FIG. 7 depicts the use of a network (such as the Internet) for exchanging data, the embodiments described and/or illustrated herein are not limited to the Internet or any particular network-based environment.

In at least one embodiment, all or a portion of one or more of the exemplary embodiments disclosed herein may be encoded as a computer program and loaded onto and executed by server 740, server 745, storage devices 760(1)-(N), storage devices 770(1)-(N), storage devices 790(1)-(N), intelligent storage array 795, or any combination thereof. All or a portion of one or more of the exemplary embodiments disclosed herein may also be encoded as a computer program, stored in server 740, run by server 745, and distributed to client systems 710, 720, and 730 over network 750.

As detailed above, computing system 610 and/or one or more components of network architecture 700 may perform and/or be a means for performing, either alone or in combination with other elements, one or more steps of an exemplary method for assessing levels of personal risk.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

In some examples, all or a portion of exemplary system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of exemplary system 100 in FIG. 1 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of exemplary system 100 in FIG. 1 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of exemplary system 100 in FIG. 1 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of exemplary system 100 in FIG. 1 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of exemplary system 100 in FIG. 1 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

According to some examples, all or a portion of exemplary system 100 in FIG. 1 may represent portions of, communicate with, and/or receive protection from one or more systems for endpoint security. As used herein, the term "endpoint security" may refer to the protection of endpoint systems from unauthorized and/or illegitimate use, access, and/or control. Examples of systems for endpoint protection may include, without limitation, anti-malware systems, user authentication systems, encryption systems, privacy systems, spam-filtering services, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

While various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

In addition, one or more of the modules described herein may transform data, physical devices, and/or representations of physical devices from one form to another. For example, one or more of the modules recited herein may receive initial information that describes a location and/or a medical state of a user, transform the initial information into an expected state that describes an expected location and/or medical state of the user, and store the initial information and/or the expected state in a database. Further, one or more of the modules recited herein may receive additional information that describes the user at a subsequent point in time, compare the additional information to the previously determined expected state, transform a result of the comparison into a risk score, and perform a safety action based on the risk score. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A computer-implemented method for assessing levels of personal risk, at least a portion of the method being performed by a computing device comprising at least one processor, the method comprising:

collecting, from at least one computing system, initial information that describes a user at an initial period of time;

determining, based at least in part on the initial information, an expected state of the user, the expected state comprising an expected medical state and an expected location;

receiving, from the computing system, additional information that describes the user at a subsequent period of time after the initial period of time, the additional information comprising an additional medical state and an additional location;

calculating a risk score by comparing the additional information with the expected state to determine a degree of divergence from the expected state, the risk score comprising a single value that indicates an aggregated combination of the following as inputs:
  a degree of divergence between the additional medical state and the expected medical state;
  a degree of divergence between the additional location and the expected location;
  a degree of divergence between at least one wireless-enabled computing device found in proximity to the user at the subsequent period of time and at least one wireless-enabled computing device expected to be found in proximity to the user;

performing a safety action based on the risk score in response to determining that the single value of the risk score satisfies a predetermined threshold, the safety action comprising the computing system transmitting a security notification to a guardian of the user.

2. The method of claim 1, wherein:
the additional medical state comprises heart rate information and is collected by a wearable computing system that tracks a medical state of the user;
the additional location is collected by a smart phone of the user that is separate from the wearable computing system;
the wireless-enabled computing device found in proximity to the user at the subsequent period of time is found by the smart phone.

3. The method of claim 1, wherein the computing system comprises a smart computing system that tracks a location of the user using at least one of:
  a global geo-positioning network;
  an indoor positioning system;
  a Wi-Fi-based positioning system.

4. The method of claim 1, wherein determining the expected state of the user further comprises extracting a user-annotated event that describes a planned location associated with a planned time.

5. The method of claim 4, wherein extracting the user-annotated event further comprises scanning one of:
  an e-mail inbox;
  a text-message conversation;
  social media.

6. The method of claim 1, wherein the computing system comprises a smart phone.

7. The method of claim 1, wherein calculating the risk score further comprises comparing the additional information to a risk map that identifies known regions of dangerous activity.

8. The method of claim 1, wherein calculating the risk score further comprises determining whether the additional location is a known location.

9. The method of claim 1, wherein the computing system comprises a smart watch.

10. The method of claim 1, wherein calculating the risk score further comprises:
- calculating an expected heart rate of the user by determining an average heart rate;
- determining a degree of divergence between the additional medical state of the user and the average heart rate.

11. The method of claim 1, wherein:
- the initial information comprises a list of expected wireless-enabled computing devices that represents wireless-enabled computing devices that are expected to be found in proximity to the user;
- the additional information comprises a list of discovered wireless-enabled computing devices that represents wireless-enabled computing devices that are discovered in proximity to the user.

12. The method of claim 11, wherein calculating the risk score further comprises comparing the list of discovered wireless-enabled computing devices to the list of expected wireless-enabled computing devices.

13. The method of claim 1, wherein the safety action further comprises at least one of:
- requesting medical aid to the user's location;
- notifying a public safety center;
- notifying the user.

14. The method of claim 1, wherein the expected medical state corresponds to at least one of:
- the user's heart rate;
- the user's respiratory rate;
- the user's blood pressure.

15. A system for assessing levels of personal risk, the system comprising:
- a collection module, stored in memory, that collects, from at least one computing system, initial information that describes a user at an initial period of time;
- a determination module, stored in memory, that determines, based at least in part on the initial information, an expected state of the user, the expected state comprising an expected medical state and an expected location;
- a reception module, stored in memory, that receives, from the computing system, additional information that describes the user at a subsequent period of time after the initial period of time, the additional information comprising an additional medical state and an additional location;
- a calculation module, stored in memory, that calculates a risk score by comparing the additional information with the expected state to determine a degree of divergence from the expected state, the risk score comprising a single value that indicates an aggregated combination of the following as inputs:
  - a degree of divergence between the additional medical state and the expected medical state;
  - a degree of divergence between the additional location and the expected location;
  - a degree of divergence between at least one wireless-enabled computing device found in proximity to the user at the subsequent period of time and at least one wireless-enable computing device expected to be found in proximity to the user;
- a safety module, stored in memory, that performs a safety action based on the risk score in response to determining that the single value of the risk score satisfies a predetermined threshold, the safety action comprising the computing system transmitting a security notification to a guardian of the user;
- at least one physical processor configured to execute the collection module, the determination module, the reception module, the calculation module, and the safety module.

16. The system of claim 15, wherein the computing system comprises a wearable computing system that tracks a medical state of the user.

17. The system of claim 15, wherein the computing system comprises a smart computing device that tracks a location of the user using at least one of:
- a global geo-positioning network;
- an indoor positioning system;
- a Wi-Fi-based positioning system.

18. The system of claim 15, wherein the determination module further determines the expected state of the user by extracting a user-annotated event that describes a planned location associated with a planned time.

19. The system of claim 18, wherein the determination module extracts the user-annotated event by scanning one of:
- an e-mail inbox;
- a text-message conversation;
- social media.

20. A non-transitory computer-readable medium comprising one or more computer-readable instructions that, when executed by at least one processor of a computing device, cause the computing device to:
- collect, from at least one computing system, initial information that describes a user at an initial period of time;
- determine, based at least in part on the initial information, an expected state of the user, the expected state comprising an expected medical state and an expected location;
- receive, from the computing system, additional information that describes the user at a subsequent period of time after the initial period of time, the additional information comprising an additional medical state and an additional location;
- calculate a risk score by comparing the additional information with the expected state to determine a degree of divergence from the expected state, the risk score comprising a single value that indicates an aggregated combination of the following as inputs:
  - a degree of divergence between the additional medical state and the expected medical state;
  - a degree of divergence between the additional location and the expected location;
  - a degree of divergence between at least one wireless-enabled computing device found in proximity to the user at the subsequent period of time and at least one wireless-enabled computing device expected to be found in proximity to the user;
- perform a safety action based on the risk score in response to determining that the single value of the risk score satisfies a predetermined threshold, the safety action comprising the computing system transmitting a security notification to a guardian of the user.

* * * * *